United States Patent [19]

Geary

[11] Patent Number: 5,421,814
[45] Date of Patent: Jun. 6, 1995

[54] HEMODIALYSIS INFUSION PORT AND ACCESS NEEDLE

[75] Inventor: Gregory L. Geary, Portland, Oreg.

[73] Assignee: Innovations for Access, Inc., West Linn, Oreg.

[21] Appl. No.: 71,577

[22] Filed: Jun. 3, 1993

[51] Int. Cl.⁶ .......................................... A61M 37/00
[52] U.S. Cl. ........................................ 604/4; 604/175;
        604/89; 604/91; 604/416
[58] Field of Search ................ 604/29, 52, 4, 5, 8,
        604/9, 93, 175, 236, 256, 91, 89, 416

[56] References Cited

U.S. PATENT DOCUMENTS

| | | | |
|---|---|---|---|
| 2,841,145 | 7/1958 | Epps | 604/89 |
| 4,421,507 | 12/1983 | Bokros . | |
| 4,506,691 | 3/1985 | Tseo | 604/91 |
| 4,581,020 | 4/1986 | Mittleman . | |
| 4,609,369 | 9/1986 | Ball | 604/89 |
| 4,632,671 | 12/1986 | Dalton . | |
| 4,639,247 | 1/1987 | Bokros . | |
| 4,645,495 | 2/1987 | Vaillancourt . | |
| 4,673,394 | 6/1987 | Fenton, Jr. et al. . | |
| 4,692,146 | 9/1987 | Hilger . | |
| 4,710,174 | 12/1987 | Moden et al. . | |
| 4,710,176 | 12/1987 | Quick . | |
| 4,755,173 | 7/1988 | Konopka et al. . | |
| 4,813,939 | 3/1989 | Marcus . | |
| 4,822,341 | 4/1989 | Colone . | |
| 4,861,341 | 8/1989 | Woodburn . | |
| 4,892,518 | 1/1990 | Cupp et al. . | |
| 4,955,861 | 9/1990 | Enegren et al. . | |
| 5,090,954 | 2/1992 | Geary . | |
| 5,167,638 | 12/1992 | Felix et al. | 604/175 |
| 5,238,582 | 8/1993 | Hori et al. | 604/416 |

Primary Examiner—Paul Prebilic
Attorney, Agent, or Firm—Robert L. Harrington

[57] ABSTRACT

An infusion port for subcutaneous placement and dialysis procedures is shown and described as including two chambers, two corresponding large area membrane access panels, and two corresponding barbs providing access between the infusion port and a patient's blood circulatory system. A valve selectively couples the chambers and the barbs in one state, and in another state isolates the barbs and couples directly the two chambers. The valve can operate externally by pressure applied to patient's skin. Hemodialysis is performed in the first state, and in the second state the port is flushed clean of residual blood by injecting cleansing fluid into one chamber and withdrawing it from the other. Also disclosed, an access needle includes a tube carrying a removable penetration pin. The tube fluidly couples to an external barb. The needle is fluidly coupled to the infusion port by driving the needle through the skin of the patient and membrane of the infusion port.

14 Claims, 5 Drawing Sheets

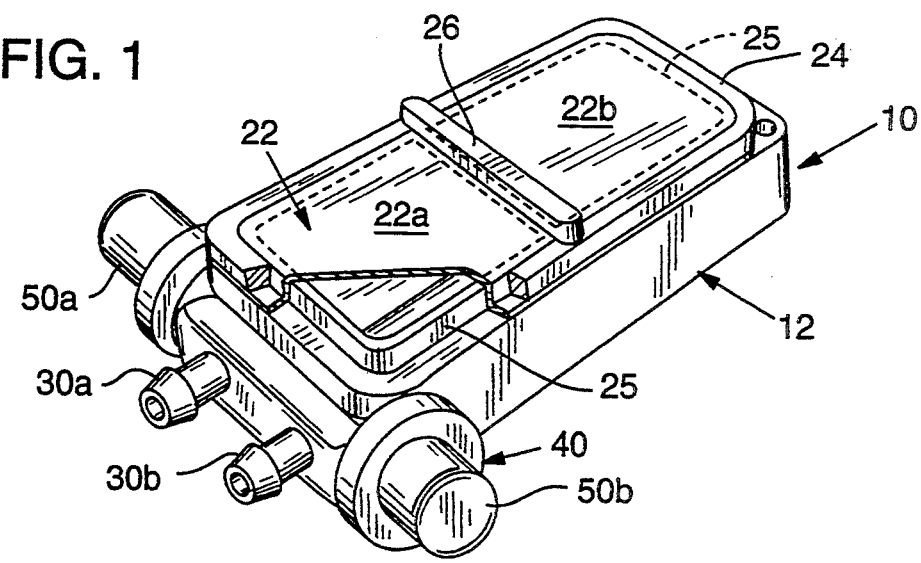
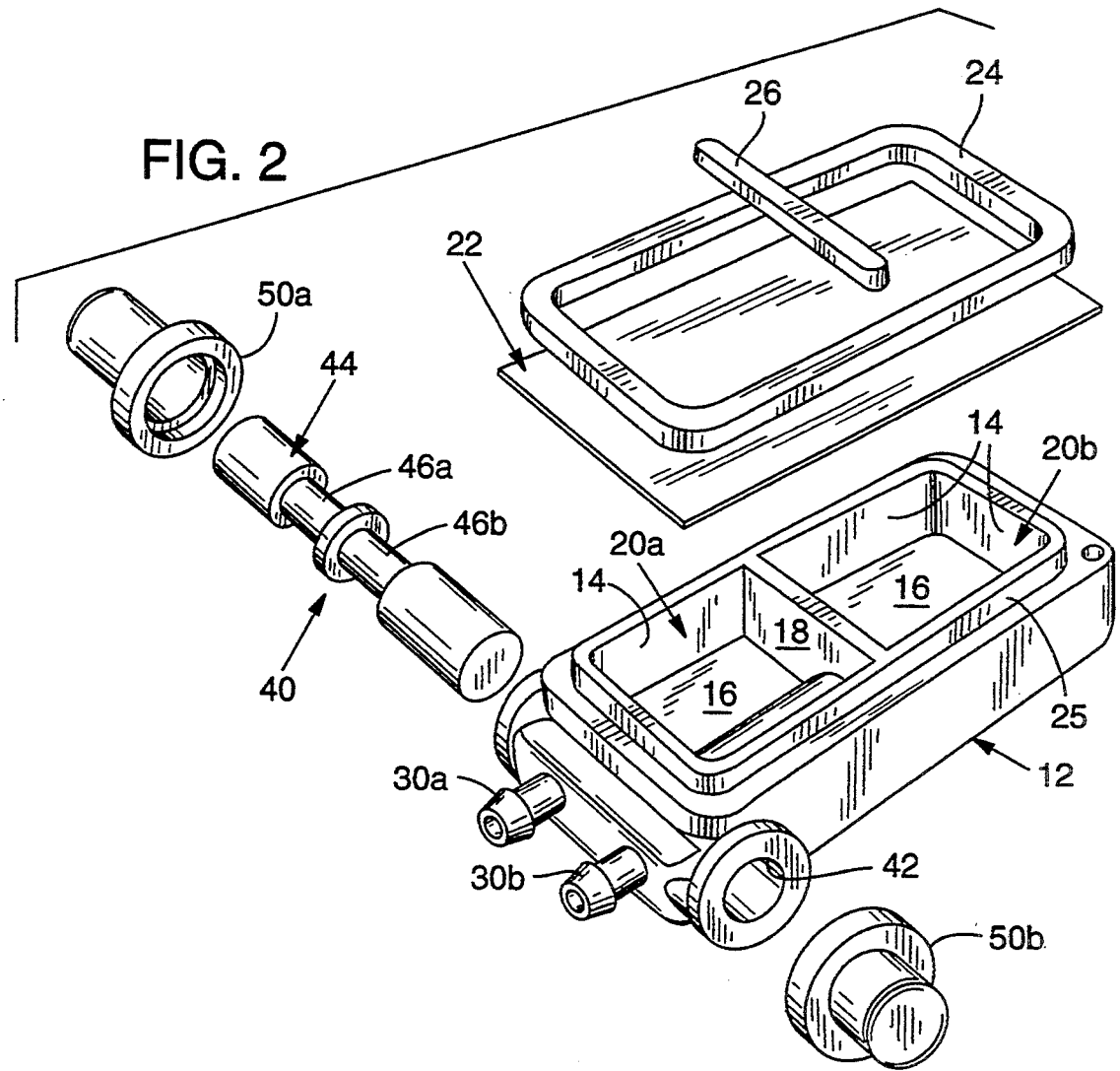

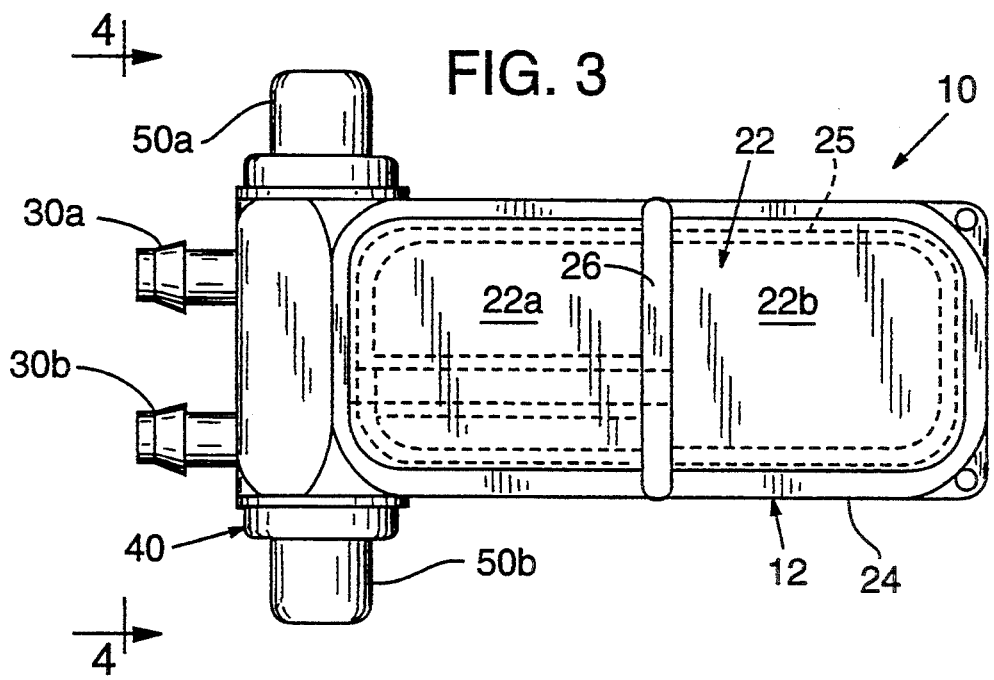
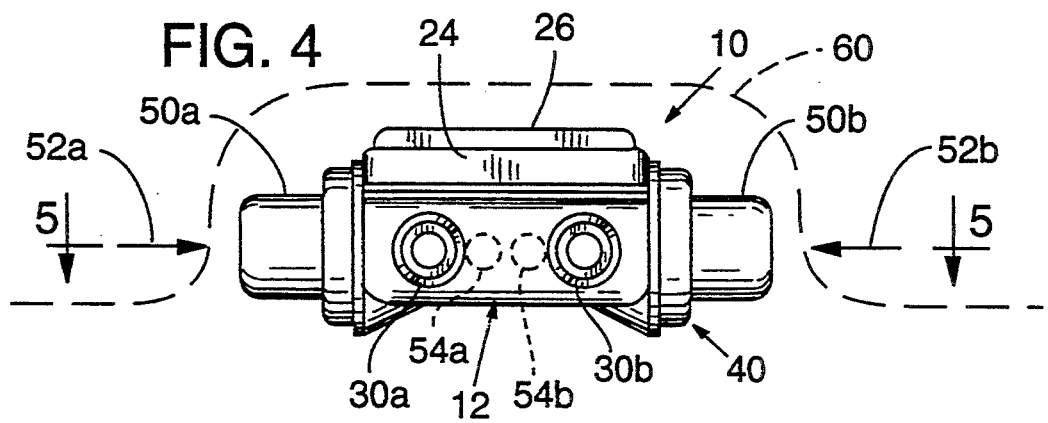
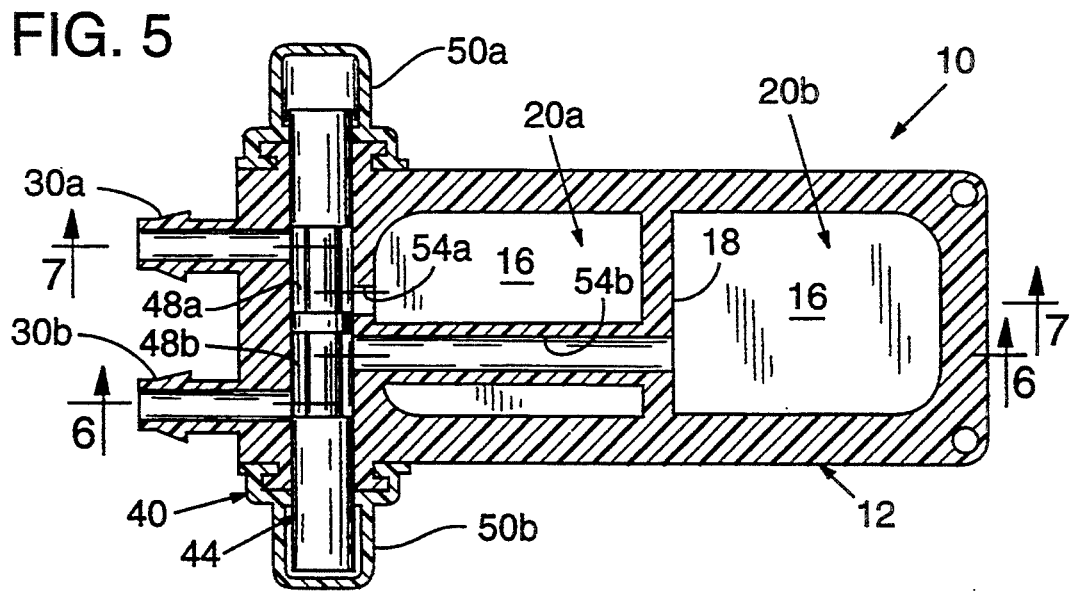

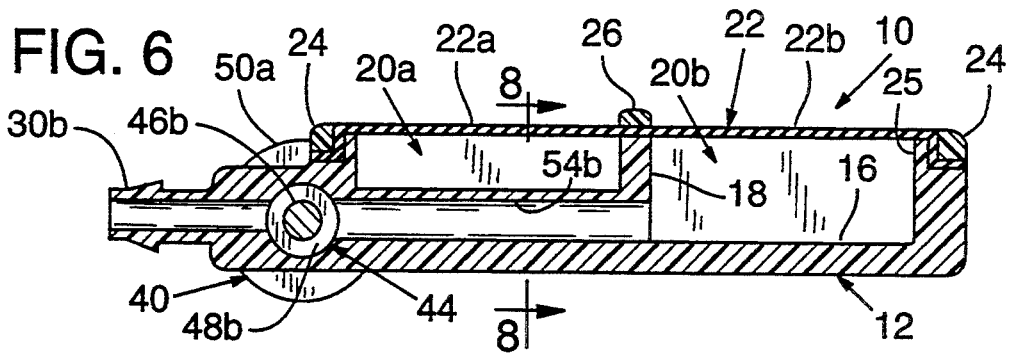
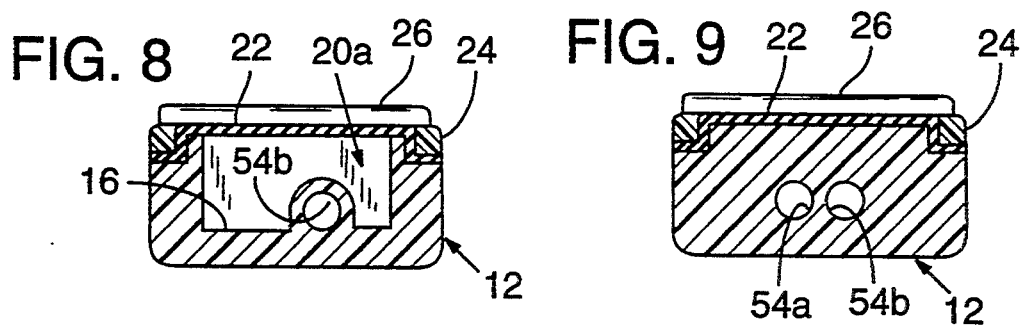
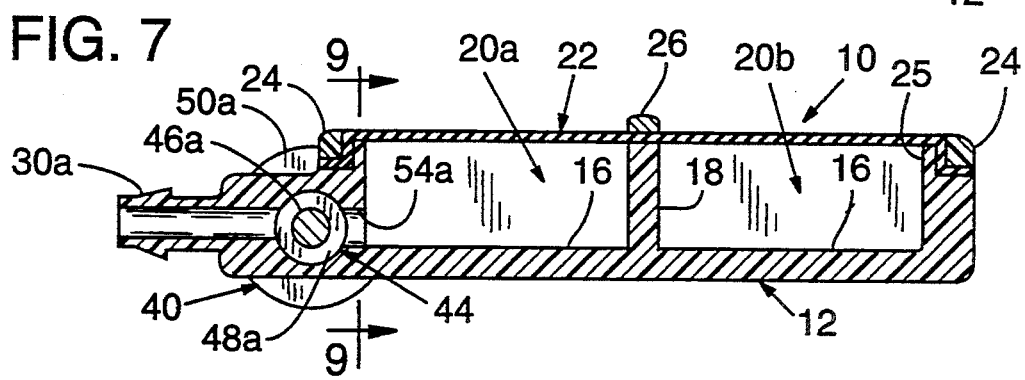
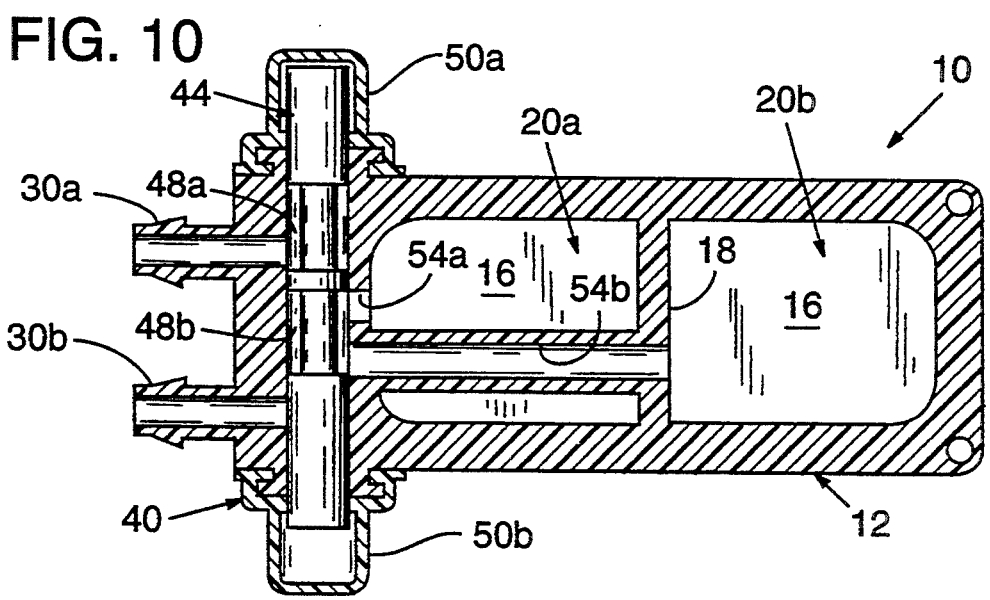

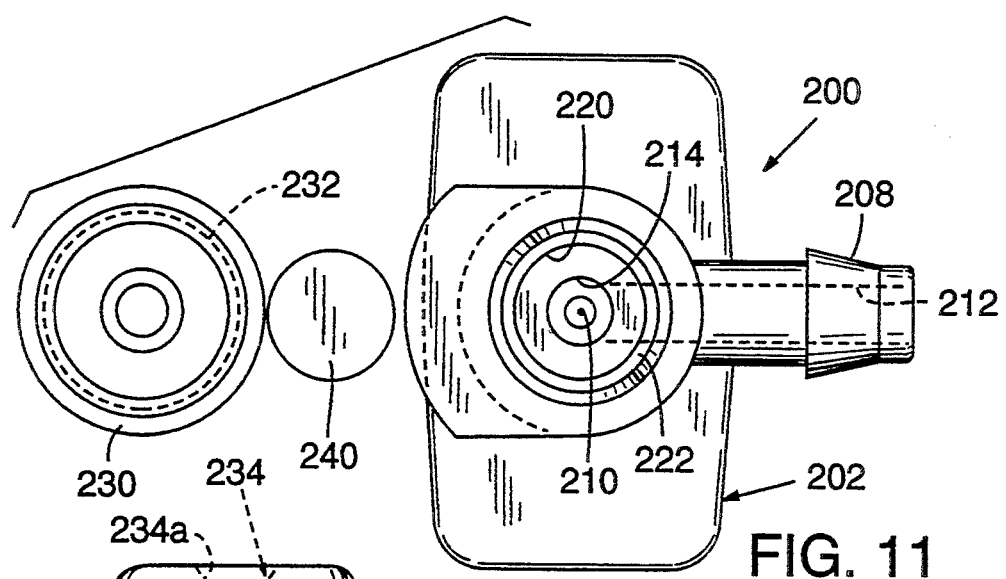
FIG. 11
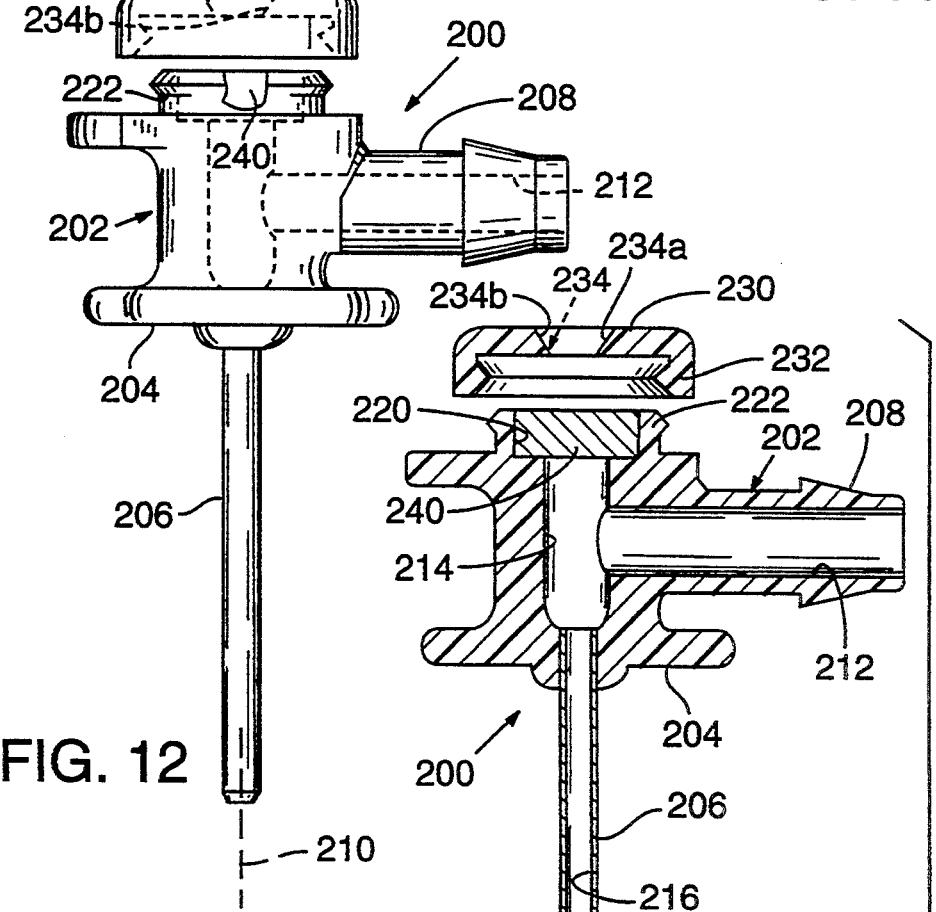
FIG. 12
FIG. 13

HEMODIALYSIS INFUSION PORT AND ACCESS NEEDLE

BACKGROUND OF THE INVENTION

The present invention relates generally to medical devices for accessing a blood circulatory system, and particularly to an infusion port subcutaneously implanted within a patient's body for aiding in hemodialysis procedures.

Certain medical procedures require access to a patient's blood circulatory system. Such access has been by way of needle directly into a patient's vein, artery, or a graph incorporated into the blood circulatory system. For example, a person suffering kidney impairment cannot maintain a clean blood supply and must have their blood supply cleansed by hemodialysis, i.e., by use of an artificial kidney machine. In such procedure, the kidney machine is temporarily integrated into the blood circulatory system to remove blood carrying impurities collected from body organs and tissues; filter that blood within the artificial kidney machine; and return the cleansed blood to the circulation system for delivery to the body organs and tissues in the normal course. The blood may be taken from a vein at one point, cleansed, and then returned to the vein at a downstream location. Blood is thereby removed from the body, cleansed, and concurrently returned to the body. The dialysis procedure is performed approximately every other day.

Repeated access to the blood system by needles damages the person's veins and arteries. Devices better withstanding repeated needle access have been placed under the patient's skin. In some cases grafts are used as an access point into the patient's blood circulatory system. Such grafts are typically placed in the person's arm. Unfortunately, repeated access to the arm graft results in skin damage along the arm.

Peritoneal dialysis is an alternative to hemodialysis. Under peritoneal dialysis, a transcutaneous tube fluidly couples at an interior end to the peritoneal cavity and an exterior end of the tube remains outside the person's body. A carrier fluid is delivered by way of this tube into the peritoneal cavity and, by process of osmosis, blood impurities are drawn into the peritoneal cavity. The carrier fluid is then removed from the peritoneal cavity by way of the catheter.

Hemodialysis, i.e., blood exchange by direct coupling to the blood circulatory system, is sometimes performed by use of catheters having one end exterior of the body and the other coupled to the blood circulatory system. Hemodialysis is performed by coupling the exterior ends of the transcutaneous catheters to an artificial kidney machine for access to the body circulatory system to draw blood from and return blood to the person's blood circulatory system.

Use of transcutaneous catheters, however, presents several problems. First of all, such catheters contribute to potential chronic contamination at their exit site. There is a significant risk of infection anytime a catheter is used in transcutaneous service. Furthermore, the personal psychological impact on a hemodialysis patient can be significant, having tubes hanging from one's body does not support a feeling of well-being and healthy outlook.

U.S. Pat. No. 5,090,954 issued Feb. 25, 1992 to applicant herein Gregory L. Geary and entitled Subcutaneous Access Device for Peritoneal Dialysis shows a peritoneal dialysis device including an elongate housing having a needle-penetrable, self-sealing outer membrane surface. The device is subcutaneously located for access in conducting peritoneal dialysis, i.e., the device is available for introducing and removing carrier fluid to and from the peritoneal cavity. The membrane of the subcutaneous device is accessed by needle and an in-dwelling catheter couples the subcutaneous device to the peritoneal cavity.

In other cases, a subcutaneous infusion port penetrated by way of a needle has been proposed for access to a patient's blood circulatory system. U.S. Pat. No. 4,892,518 issued Jan. 9, 1990 to Cupp et al and entitled Hemodialysis proposes a hemodialysis port assembly including a port and a catheter assembly. The two channel catheter assembly shown by Cupp et al is to be implanted in the chest of a patient with the two channel catheter assembly coupled to the subclavian vein. The blood flow in the vein is away from the end of the catheter assembly and each channel of the catheter assembly couples to one chamber of the port. More particularly, an upstream inlet channel of the catheter assembly couples to one chamber of the port while the downstream outlet channel of the catheter assembly couples to the other chamber of the port. In this manner, blood may be drawn from the upstream portion of the subclavian vein by way of the first chamber, cleansed by artificial kidney machine, and returned to the second chamber of the port assembly for delivery by way of the second channel of the catheter assembly at the downstream portion of the subclavian vein. Near the remote end of the catheter assembly, the inlet channel terminates in an inlet valve and the outlet channel terminates in an outlet valve, each valve being described as a "flapper" on which the blood is incident but does not impede the flow of blood in the subclavian vein. The inlet and outlet valves are spaced a sufficient distance to allow removal of impure blood at an upstream point and delivery of cleansed blood at a downstream point. The flapper valves open in response to pressure differentials. At column 1, line 65, it is suggested that the outlet valve should be a two-way valve to conduct the blood out of the vein and to the artificial kidney machine, and also to conduct a solution for cleaning the outlet channel. The inlet valve may also be, it is suggested, a two-way valve to allow cleaning with solution, if needed.

U.S. Pat. No. 4,822,341 issued Apr. 18, 1989 to Colone and entitled Vascular Access Fistula shows an implantable vascular graft communicating percutaneously through a pair of access tubes exterior of the patient's body for dialysis procedures. The external tubes are used for dialysis only after the graft heals. After healing, the tubes are surgically severed so that the apparatus is located entirely subcutaneously. A slidable, subcutaneous shutoff valve is mounted to the graft to isolate the blood flow from the external tubes just before those tubes are severed. During the tube-severing surgical procedure, the valve 22 is accessed via an incision and then permanently closed. The apparatus includes no separate reservoirs or chambers.

U.S. Pat. No. 4,692,146 issued Sep. 8, 1987 to Hilger and entitled Multiple Vascular Access Port shows a subcutaneous access arrangement including two chambers, each penetrable by hypodermic needle and a two channel catheter, each channel being coupled to one of the chambers, for providing an inlet and outlet access to a patient's blood circulatory system.

U.S. Pat. No. 4,710,174 issued Dec. 1, 1987 to Moden et al and entitled Implantable Infusion Port and U.S. Pat. No. 4,673,394 issued Jun. 16, 1987 to Fenton, Jr. et al and entitled Implantable Treatment Reservoir both show subcutaneous reservoirs similar to that shown by Hilger with a reservoir accessible by hypodermic needle and associated catheter for thereby accessing a patient's blood circulatory system.

As may be appreciated, in using an infusion port of the type described above the reservoirs and catheters often fill with the patient's blood supply during use. Certain problems exist with the post-procedure steps taken to clean or flush the device. The blood must be flushed out or removed in some fashion to avoid undesirable blood clotting within the infusion port. As noted above, the Cupp apparatus suggests that flushing be accomplished by introducing fluid into each of the chambers and forcing that fluid out through the catheter channels and into the patient's blood system. In performing such a flushing operation, it may be appreciated that the introduction of flushing solution into the infusion port should be at a conservative rate and pressure and may require some amount of time to suitably flush blood from the device.

Most of the available subcutaneous infusion ports are simply small medication delivery systems. For this purpose, these relatively smaller infusion ports are acceptable. Such ports do not, however, provide sufficient flow capacity to perform hemodialysis. For example, delivery of approximately 100 cc of medication per hour is typical when using a subcutaneous infusion port for medication delivery. Hemodialysis requires, however, much a greater volume of fluid exchange, typically up to 400 cc per minute of blood flow to with the artificial kidney machine. Thus, most infusion ports are not acceptable for the relatively high volume flow required for hemodialysis procedures. According to present medical practice, hemodialysis is not performed by use of infusion ports. Hemodialysis is, according to conventional modern practice, performed using either a graft placed in the patient's arm, or by using transcutaneous catheters having one end maintained external of the person's body for the required frequent access to the blood circulatory system.

It is desirable, therefore, that a subcutaneous infusion port be more readily adapted for high volume capacity required of hemodialysis procedures and well adapted for flushing without the limitation of relatively small flow rates and pressure magnitudes of the cleansing solution.

SUMMARY OF THE INVENTION

In accordance with a preferred embodiment of the present invention, a subcutaneous infusion port includes two chambers, each including a membrane panel accessible by way of a needle, and corresponding conduits from each chamber coupling to catheters attached to the patient's blood circulatory system. The apparatus according to the present invention further includes a valve arrangement intermediate of the chambers and the catheters whereby communication of fluids between the chambers and corresponding catheters and between the chambers themselves may be selectively controlled. In the preferred embodiment of the present invention, a two-state valve between the infusion port chambers and the catheters provides these functions. In a first state, the valve couples each chamber to its corresponding catheter for dialysis procedures wherein blood is removed by way of one chamber and, after cleansing, returned to the other chamber. In a second state, the valve isolates the chambers from the catheters and also couples the two chambers for direct fluid flow therebetween. Thus, to flush the infusion port of the present invention, the two-way valve is placed in its second state, cleansing fluid is introduced into one chamber and concurrently removed from the other chamber. Overall, the infusion port of the present invention is substantially larger, e.g., providing on the order of two square inches of needle penetratable membrane, and is sized to accommodate the relatively large volume flow required for hemodialysis. This arrangement also permits relatively large magnitude pressure and volume of cleansing fluid in isolation of the circulatory system to more quickly and thoroughly flush blood from the infusion port.

The present invention further provides an access needle well adapted for use in conjunction with the above-described infusion port. The access needle includes a tubular conduit carrying coaxially therein a penetration pin, with the point of the pin extending slightly beyond the distal end of the conduit. The proximal end of the conduit carries a main body with a chamber thereof providing coupling to the tubular needle conduit and to a barb structure whereby a conduit external of the body may be attached to the barb and establish fluid communication with the tubular conduit of the access needle. The needle is placed into service by penetration through the patient's skin and into the membrane of the subcutaneous infusion port. The penetration pin is then removed to establish fluid coupling between the infusion port and the external conduit attached to the access needle.

The subject matter of the present invention is particularly pointed out and distinctly claimed in the concluding portion of this specification. However, both the organization and method of operation of the invention, together with further advantages and objectives thereof, may be best understood by reference to the following description taken with the accompanying drawings wherein like reference characters refer to like elements.

BRIEF DESCRIPTION OF THE DRAWINGS

For a better understanding of the invention and to show how the same may be carried into effect, reference will now be made, by way of example, to the accompanying drawings in which:

FIG. 1 illustrates in perspective an infusion port according to a preferred embodiment of the present invention.

FIG. 2 is an exploded perspective view of the infusion port of FIG. 1.

FIG. 3 is a top view of the infusion port of FIG. 1.

FIG. 4 is an end view showing subcutaneous placement of the infusion port of FIG. 1 as taken along lines 4—4 of FIG. 3.

FIG. 5 is a sectional top view of the infusion port of FIG. 1 as taken along lines 5—5 of FIG. 4 showing a valve of the infusion port in an infusion state.

FIG. 6 is a side sectional view of the infusion port of FIG. 1 as taken along lines 6—6 of FIG. 5.

FIG. 7 is a side sectional view of the infusion port of FIG. 1 as taken along lines 7—7 of FIG. 5.

FIG. 8 is a sectional view of the infusion port of FIG. 1 as taken along lines 8—8 of FIG. 6.

FIG. 9 is a end sectional view of the infusion port of FIG. 1 as taken along lines 9—9 of FIG. 7.

FIG. 10 is a top sectional view of the infusion port of FIG. 1 similar to that shown in FIG. 5, but showing the valve in a flushing state.

FIGS. 11 and 12 are top and side views, respectively, of an access needle for use in conjunction with the infusion port of FIGS. 1-10.

FIG. 13 is a sectional view of the access needle of FIGS. 11 and 12.

DETAILED DESCRIPTION OF A PREFERRED EMBODIMENT

Figure 14:
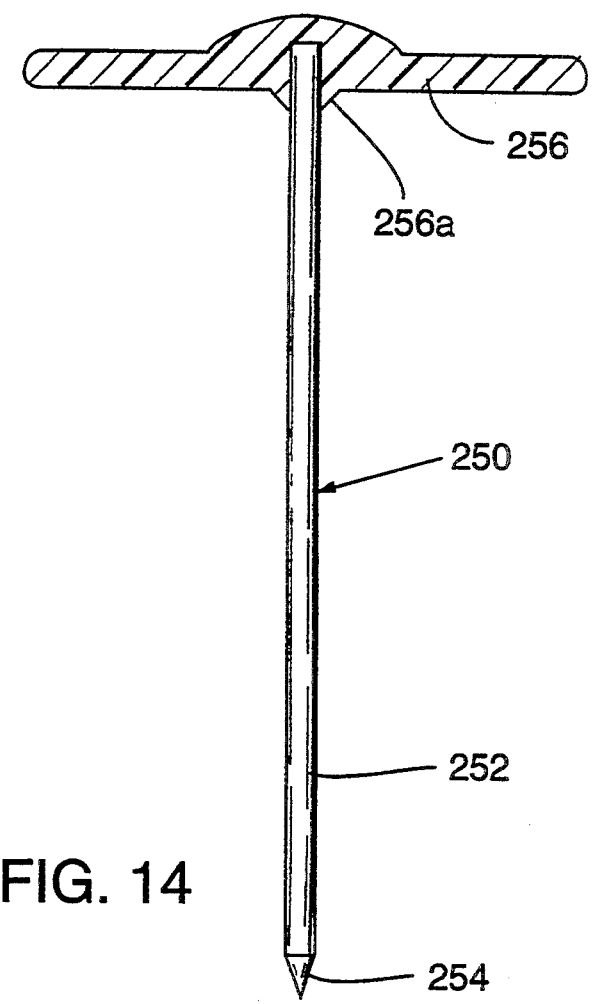
FIG. 14 is a side view of a penetration pin used in conjunction with the access needle of FIGS. 11-13.

FIG. 1 illustrates an infusion port 10 according to a preferred embodiment of the present invention. FIG. 2 shows the exploded view of the infusion port 10 and FIG. 3 is a top view of the port 10. In FIGS. 1-3, the infusion port 10 includes a chamber box 12 defining side walls 14 and floor 16. A center wall 18 (FIG. 2) in cooperation with side walls 14 and half portions of floor 16 define two chambers 20a and 20b. A membrane 22 completes the chambers 20 by resting directly upon the upper edges of side walls 14 and center wall 18. A membrane sealing frame 24 captures the membrane 22 against a frame lip 25 of the chamber box 12 and attaches to the chamber box 12 for sealing the chambers 20. Also, a sealing bar 26 lies over and along the center wall 18 and attaches to the sealing frame 24 for isolating the chambers 20a and 20b.

Thus, the membrane 22 as mounted upon the chamber box 12 by way of frame 24 and bar 26 defines two membrane access panels 22 (FIGS. 1 and 3), individually 22a and 22b, for accessing the corresponding chambers 20a and 20b by way of needle penetration through the membrane 22. It is suggested that membrane 22 be provided as medical grade needle-permeable, self-sealing elastomer material, such as silicone rubber. For example, medical grade, 60 SHORE A rubber may be used as membrane 22, however, a variety of such needle-permeable, self-sealing materials are available for this purpose.

Infusion port 10 also includes a pair of barbs 30, individually 30a and 30b, corresponding to the chambers 20a and 20b, though not directly coupled thereto. The barbs 30a and 30b provide input and output to the infusion port 10 relative to the patient's blood circulatory system.

Interposed between the chambers 20 and the barbs 30 is a bi-state spool valve 40 controllably coupling in a first state the chambers 20 to the corresponding barbs 30, i.e., the chamber 20a to the barb 30a and the chamber 20b to the barb 30b, and selectively isolating in a second state the barbs 30 from the chambers 20 while concurrently coupling the chambers 20a and 20b. The spool valve 40 thereby selectively provides in its first state a first fluid pathway between the chamber 20a and the barb 30a and a second fluid pathway between the chamber 20b and the barb 30b. In its second state, spool valve 40 isolates the barbs 30 from the corresponding chambers 20 by closing the first and second fluid pathways, and opening a third fluid pathway directly between the chambers 20a and 20b.

Spool valve 40 includes a spool cylinder 42 and a spool piston 44 slidably disposed within the cylinder 42. Spool piston 44 includes a pair of annular recess formations 46, i.e., length portions of reduced diameter, individually 46a and 46b. Thus, with the spool piston 44 slidably positioned within the spool cylinder 42, the recess formations 46a and 46b provide annular cavities 48, individually 48a and 48b, slidably positionable within the cylinder 42 according to the position of piston 44. The annular cavities 48 provide selective coupling among the barbs 30 and corresponding chambers 20, and also directly between the chambers 20a and 20b as described above.

Spool valve 40 also includes a pair of pliable sealing boots 50, individually 50a and 50b, sealably attaching to the chamber box 12 to isolate the spool cylinder 42 relative to the body cavity in which port 10 rests subcutaneously. The boots 50 are flexible rubber or plastic elements allowing the caregiver to move the piston 44 within the cylinder 42 as by pressure applied at selected ends of piston 44.

While not shown herein, the infusion port 10 may be also provided with a layer of porous material overlaying the membrane 22. Such porous material allows skin and fibroblast ingrowth therein. A suitable material is available under the trademark GOR-TEX, as a polyester resin velour, porous or expanded PTFE (polytetra-fluroethylene). Other similar porous or rough type material allowing tissue ingrowth are also potentially useful in connection with the infusion port 10. U.S. Pat. No. 5,090,954 issued Feb. 25, 1992 to applicant herein Gregory L. Geary and entitled Subcutaneous Access Device for Peritoneal Dialysis illustrates a single chamber, no valve infusion port similar to infusion port 10 shown herein to the extent of its subcutaneous placement, needle-penetrable and self-sealing membrane, and PTFE overlay. The disclosure of U.S. Pat. No. 5,090,954 is incorporated herein fully by reference.

FIG. 4 illustrates subcutaneous placement of the infusion port 10. In FIG. 4, the infusion port 10 is positioned below the skin 60 of the patient, typically in the chest area, and may be operated externally by a caregiver by pushing upon the boots 50a and 50b, by application of force to skin 60, for the purpose of sliding the piston 44 within the cylinder 42. The spool valve 40 is thereby urged into one of the two operational states. Force applied at the boot 50a, as indicated at the referenced arrow 52a, urges the spool valve 40 into an infusion state as illustrated in FIG. 5. Force applied at the boot 50b, as indicated at the reference arrow 52b, urges the spool valve 40 into a flushing state as illustrated in FIG. 10 and discussed hereinafter.

In the infusion state (FIG. 5), the barb 30a couples by of annular cavity 48a of spool valve 40 to the chamber 20a by way of conduit 54a. The barb 30b couples by way of annular cavity 48b to the chamber 20b by way of conduit 54b. FIG. 6 further illustrates the coupling of barb 30b to the chamber 20b by way of annular cavity 48b of valve 40 and conduit 54b. FIG. 7 illustrates coupling of barb 30a to chamber 20a by way of annular cavity 48a and the conduit 54. FIGS. 8 and 9 further illustrate the conduit 54 and the mounting arrangement of membrane 22, sealing frame 24, frame lip 25, and sealing bar 26 defining the chambers 20a and 20b.

FIG. 10 illustrates the valve 40 in its second state, i.e., the flushing state wherein the barbs 20 are isolated from the chambers 20 and the chambers 20a and 20b are interconnected by way of valve 40. In FIG. 10, the barb 30a is coupled to the annular cavity 48a, but annular cavity 48a in this position of valve 40 has no output channel. The barb 30b terminates at the larger diameter portion of the spool piston 44 and is thereby isolated. The annular cavity 48b, however, couples the conduit 54a and the conduit 54b coupling the chambers 20a and 20b for fluid exchange.

In the flushing state of valve 40, the chambers 20a and 20b are accessed by way of panels 22a and 22b, i.e., by way of needle penetration therethrough. Cleansing solution may be forced at relatively strong pressure and large volume into one of the chambers 20 and taken from the other one of chambers 20 because in its flushing state port 10 is well isolated from the blood circulatory system. Chambers 20a and 20b are thereby quickly and efficiently washed free of any residual blood following a dialysis procedure.

FIGS. 11 and 12 show top and side views, respectively, of an access needle 200. Access needle 200 includes a main body 202 formed by, for example, plastic injunction. Body 202 includes a downward facing skin contacting surface 204. A stainless steel sixteen gauge thin walled tube 206 extends downward, in the view of FIGS. 12 and 13, from the surface 204. In the illustrated embodiment, tube 204 extends approximately 0.87 inches below the surface 204. Body 202 includes a barb 208 extending laterally outward relative to the central axis 210 of tube 206. Barb 208 defines a conduit 212 fluidly coupled to a central chamber 214 of body 202. Conduit 216, defined by tube 206, is also fluidly coupled to the chamber 214. A fluid coupling thereby exists between the conduit 212 of barb 208 and the conduit 216 of tube 206, by way of chamber 214. An upper cylindric chamber 220 of body 202 lies directly above the chamber 214, being defined by a male annular snap formation 222. A cap 230, including a downward extending female annular snap formation 232, attaches to the snap formation 222 of body 202.

Cavity 220 is dimensioned to closely receive a cylindric silicon rubber plug 240. Once plug 240 is positioned within cavity 220, cap 230 attaches by snap formations 222 and 232 to body 202 to retain plug 240 therein. Plug 240 may be of the same type of needle-penetrable, self-sealing medical grade silicon rubber as described above in connection with membrane 22 for port 10.

Cap 230 further includes a generally conic centrally located aperture 234, having an upper diameter 234a greater than a lower diameter 234b. The needle 200 is assembled by placing the plug 240 within the chamber 220 and securing the cap 230 to the body 202.

FIG. 14 illustrates a penetration pin 250 providing a skin and infusion port membrane penetration function for the needle of FIGS. 11-13. Penetration pin 250 includes a shaft 252 having a sharpened non-coring tip 254. Tip 254 may be provided as a conic ground tip, or may be in the form of a trocar tip. Opposite tip 254, shaft 252 carries a generally flat handle 256. Handle 256 includes a generally conic downward protruding structure 256a corresponding in shape and dimension to the aperture 234 of cap 230 and surrounding shaft 252. The penetration pin 250 is added to the assembly of needle 200 by piercing, with tip 254, the plug 240 and driving the shaft 252 along the central axis 210 until the conic structure 256 of handle 256 rests within the conic aperture 234 of cap 230. The shaft 252 is dimensioned in length with respect to the distance between cap 230 and the distal end 206a of tube 206 such that tip 254 extends slightly beyond tube 206 as a skin tissue and infusion port membrane penetrating structure.

The completed assembly of needle 200 and penetration pin 250 pierces skin 60 (FIG. 4) to access a subcutaneous infusion port 10. More particularly, by applying downward force to the handle 256 of penetration pin 250 the entire assembly of pin 250 and needle 200 passes through skin 60 and a membrane of infusion port 10. Once the assembly of needle 200 and penetration pin 250 engages infusion port 10, the penetration pin 250 is withdrawn from needle 200. As may be appreciated, the plug 240 is self-sealing upon withdrawal of shaft 252 therefrom. In this manner, tube 206 is fluidly coupled to a chamber of infusion port 10. As a result, the barb 208, and particularly the conduit 212 thereof, is fluidly coupled by way of chamber 214 of body 202 and conduit 216 of tube 206 to a chamber of infusion port 10. Thus, a bi-directional fluid pathway is established between an external catheter and an in-dwelling catheter attached to a barb 30 of port 10. For withdrawing fluid from subcutaneous infusion port 10, it is suggested that tube 206 include near the distal end 206a side ports or apertures (not shown) to maintain fluid flow into tube 206 should distal end 206a be brought against the chamber floor.

Figure 15:
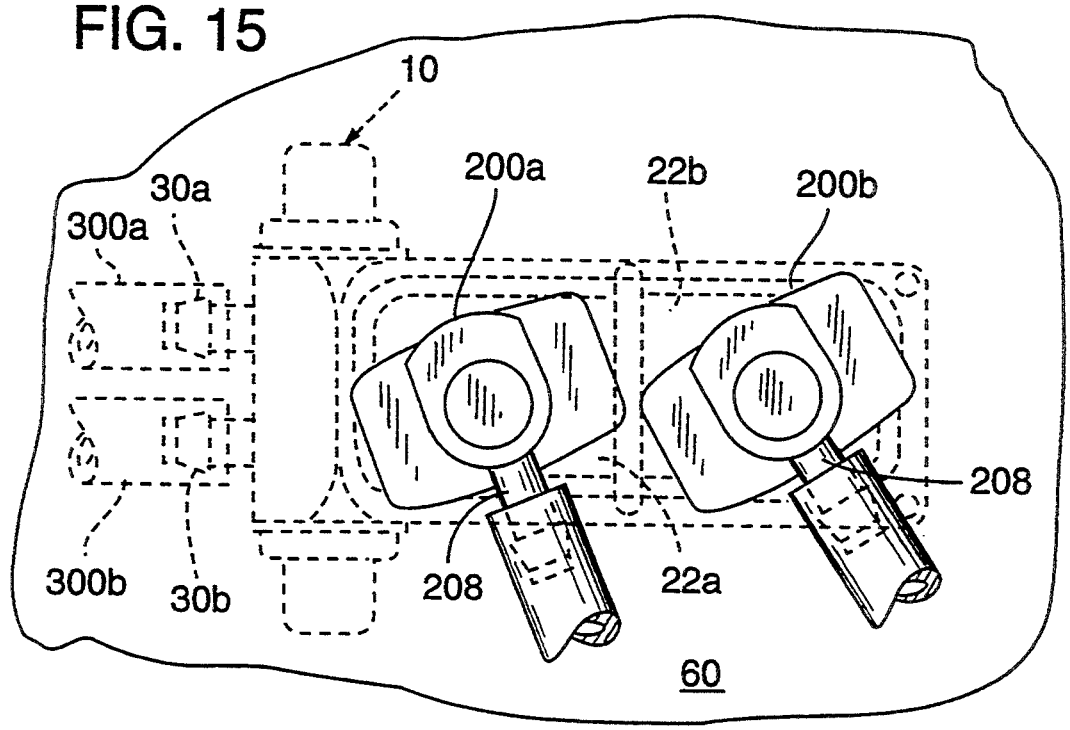
FIG. 15 illustrates use of a pair of access needles as illustrated in FIGS. 11-14 in conjunction with the dual-chamber access port of FIGS. 1-10.

FIG. 15 illustrates use of two needles 200, individually 200a and 200b, fluidly coupled to the respective chambers 20a and 20b, respectively, of the above described dual chamber infusion port 10. Each of needles 200a and 200b is fluidly coupled by penetration of the corresponding panels 22a and 22b of membrane 22 as described above in connection with FIGS. 15 and 16. In this manner, the barbs 208a and 208b, external of the skin 60 are fluidly coupled to the barbs 30a and 30b, respectively, of the port 10 when portion 10 is placed in its infusion state. Hemodialysis may then be performed relative to in-dwelling catheters 30a and 30b, attached to barbs 30a and 30b, respectively. Injection and withdrawal of bodily fluids relative by way of the external barbs 208a and 208b is then accomplished in conventional fashion. Furthermore, by operation of the spool valve 40, the chambers 208a and 208b may be flushed by injection and withdrawal of fluid relative to the external barbs 208a and 208b. More particularly, the spool valve 40 is placed in its flushed state directly connecting the chambers 20a and 20b. The external barbs 208a and 208b are directly coupled to the respective chambers 20a and 20b. By flushing fluid into one of barbs 208 and withdrawing fluid from the other one of barbs 208, the port 10 can be quickly and thoroughly flushed clean of any residual blood. As may be appreciated, such flushing procedure is performed in isolation of any body vessels or cavities, and thereby may be performed with greater fluid pressure and volume, and therefore more quickly, efficiently, and more comfortably for the patient.

In overall operation as a hemodialysis infusion port, port 10 is subcutaneously placed with the barbs 30a and 30b coupled by way of respective in-dwelling catheters to appropriate locations in the patient's blood circulatory system. The needles 200 are then fluidly coupled to the chambers 20a and 20b as illustrated above in FIG. 15. At this point, the valve 40 is moved to its infusion state, i.e., coupling the chambers 20a and 20b with the corresponding barbs 30a and 30b. The chambers 20a and 20b may then be aspirated by pulling blood out of the body through needles 200a and 200b, e.g., by way of hypodermic needle fluidly coupled to the corresponding barbs 208a and 208b. This insures that the port 10 is properly coupled to the blood circulatory system. The needles 200a and 200b are then appropriately coupled to an artificial kidney machine by way of catheters attached to corresponding barbs 208a and 208b. The artificial kidney machine is then activated and hemodialysis performed by withdrawing blood through one of needles 200 and returning blood by way of the other one of needles 200.

Following dialysis, needles 200 are disconnected from the artificial kidney machine, but remain in the chambers 20 of infusion port 10. At this point, the infusion port 10 is flushed free of blood by forcing saline into both chambers 20a and 20b by way of the corresponding needles 200a and 200b. A volume of saline at least equal to the capacity of chambers 20a and 20b and the catheters coupling infusion port 10 and the patient's blood system is forced into port 10. This substantially removes all blood from the assembly. In other words, all the blood in the port 10 and associated in-dwelling catheters is pushed back into the blood circulatory system and replaced with saline.

The valve 40 is then switched to its flushing state. The caregiver injects saline into one of chambers 20 by way of the corresponding needle 200 and removes saline by way of the other needle 200. This procedure is performed in isolation of the blood circulatory system and may be executed at relatively large volume and pressure without introducing such cleansing fluid into the patient's blood circulatory system. In this manner, a thorough, complete cleaning of blood from the infusion port 10 results. The needles 200 are then removed from the patient and the port 10 is left in its flushing mode, i.e., left with the chambers 20 directly coupled and isolated from the blood circulatory system. If necessary, a mixture of heprine may be left in the infusion port 10 to insure that no blood clotting occurs therein. The catheters remain filled with saline following the hemodialysis procedure, as is common practice with other hemodialysis procedures.

It will be appreciated that the present invention is not restricted to the particular embodiment that has been shown and described herein and that variations may be made therein without departing from the scope of the invention as found in the appended claims and the equivalence thereof.

What is claimed is:

1. An infusion port comprising: an infusion box including first and second chambers each accessible by way of corresponding first and second membranes each members penetrable by a hypodermic needle;
   first and second barbs each for providing fluidic access between one of the first and second chambers, respectively, of the infusion port and a patient's blood circulatory system; and
   a valve interposed between said barbs and said chambers for selectively coupling fluid communication in a first mode between said first barb and said first chamber and between said second barb and said second chamber, and in a second mode said valve both providing for fluidic communication between said first and second chambers and providing fluidic isolation between said first and second chambers and said first and second barbs.

2. A port according to claim 1 wherein said valve is a spool valve operable by a pushing force applied thereto when said port is subcutaneously positioned.

3. A port according to claim 1 wherein said infusion port has a volume capacity sufficient to accomplish blood transfer therethrough for hemodialysis procedures.

4. A port according to claim 1 wherein said membranes are medical grade silicon rubber suitable for subcutaneous placement.

5. A port according to claim 1 further comprising an access needle comprising:
   a main body including a main chamber;
   a barb fluidically coupled to said main chamber;
   a tube fluidically coupled to said main chamber;
   a needle penetrable self-sealing member covering the main chamber; and
   a penetration pin slidably resting co-axially within said tube with a penetration tip extending beyond a distal end of said tube, said penetration pin having a shaft passing through said self-sealing member whereby said tip may be employed to fluidically couple said distal end of said tube with at least one of said first and second chambers by penetration of the corresponding membrane with said tip and removal of said pin shaft from said self-sealing member.

6. An infusion port comprising:
   an infusion box including first and second infusion chambers, each accessible by way of corresponding membranes by way of hypodermic needles;
   first and second access barbs for providing fluidic access between the infusion port and a patient's blood circulatory system; and
   a valve interposed between said barbs and said chambers for selectively coupling fluid communication therebetween, said valve operating in a first state fluidically coupling the first barb to the first chamber and the second barb to the second chamber, and said before operating in a second which both fluidically isolates said barbs from said chambers and fluidically couples said chambers.

7. A port according to claim 6 wherein said valve is a spool valve operable by a pushing force applied thereto when said port is subcutaneously positioned.

8. A port according to claim 6 wherein said infusion port has a volume capacity sufficient to accomplish blood transfer therethrough for hemodialysis procedures.

9. A port according to claim 6 wherein said membrane is medical grade silicon rubber suitable for subcutaneous placement.

10. A port according to claim 6 further comprising a pair of access needles, at least one of said needles comprising:
    a main body including a main chamber;
    a barb fluidically coupled to said main chamber;
    a tube fluidically coupled to said main chamber;
    a needle penetrable self-sealing member; and
    a penetration pin slidably resting co-axially within said tube with a penetration tip extending beyond a distal end of said tube, said penetration pin having a shaft passing through said self-sealing member whereby said tip may be employed to fluidically couple said distal end of said tube with at least one of said first and second chambers by penetration of said corresponding membrane with said tip and removal of said pin shaft from said self-sealing member.

11. A hemodialysis infusion port for subcutaneous placement and repeated access to a patient's blood circulatory system, the port comprising:
   first and second chambers each of volume sufficient to conduct blood therethrough in execution of hemodialysis, each chamber being defined in part by corresponding needle penetrable and self-sealing first and second access membranes;
   first and second coupling members for fluid coupling of indwelling catheters to first and second chambers, respectively; and
   a valve interposed between said chambers and said coupling members and operable to selectively fluidically couple each chamber to a corresponding one of said coupling members, said valve providing at least two modes of operation, a first mode of operation fluidically coupling each chamber to a corresponding one of said coupling members, a second mode of operation both fluidically isolating said chambers and the corresponding coupling members and fluidically coupling said first and second chambers.

12. A port according to claim 11 further comprising a pair of access needles, at least one of said needles comprising:
   a main body including a main chamber;
   a barb fluidically coupled to said main chamber;
   a tube fluidically coupled to said main chamber;
   a needle penetrable self-sealing member covering the main chamber; and
   a penetration pin slidably resting co-axially within said tube with a penetration tip extending beyond a distal end of said tube, said penetration pin having a shaft passing through said self-sealing member whereby said tip may be employed to fluidically couple said distal end of said tube with at least one of said first and second chambers by penetration of said corresponding membrane with said tip and removal of said pin shaft from said self-sealing member.

13. A port according to claim 11 wherein said first and second membranes comprise self-sealing medical grade silicon rubber.

14. A port according to claim 11 wherein said valve is a spool valve operable by a pushing force applied thereto when said port is subcutaneously positioned.

* * * * *

UNITED STATES PATENT AND TRADEMARK OFFICE
CERTIFICATE OF CORRECTION

PATENT NO. : 5,421,814
DATED : June 6, 1995
INVENTOR(S) : Geary

It is certified that error appears in the above-indentified patent and that said Letters Patent is hereby corrected as shown below:

Claim 1: Col. 9, line 52, replace "members" with --membrane--.

Claim 6: Col. 10, line 38, change "before" to --valve--; after "second" insert --state--.

Signed and Sealed this

Fifteenth Day of August, 1995

Attest:

BRUCE LEHMAN

Attesting Officer

Commissioner of Patents and Trademarks